US006410592B1

(12) United States Patent
Gibson et al.

(10) Patent No.: US 6,410,592 B1
(45) Date of Patent: Jun. 25, 2002

(54) AMINOMETHYLCARBOXYLIC ACID DERIVATIVES

(75) Inventors: S. G. Gibson; D. R. Jaap, both of Scotland; S. N. Thorn, England; R. R. Gilfillan, Scotland, all of (GB)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 09/744,520

(22) PCT Filed: Jul. 26, 1999

(86) PCT No.: PCT/EP99/05477

§ 371 (c)(1),
(2), (4) Date: Jan. 25, 2001

(87) PCT Pub. No.: WO00/07978

PCT Pub. Date: Feb. 17, 2000

(30) Foreign Application Priority Data

Jul. 31, 1998 (EP) .............................................. 98306149

(51) Int. Cl.$^7$ ........................ A01N 37/12; A01N 37/44; A01N 43/42; A61K 31/24; A61K 31/47
(52) U.S. Cl. ...................... 514/539; 514/82; 514/100; 514/187; 514/311; 560/37; 560/100; 546/165
(58) Field of Search .................. 514/82, 100, 187, 514/311, 539; 560/19; 546/165

(56) References Cited

U.S. PATENT DOCUMENTS 5,977,136 A * 11/1999 Di Fabio et al. ............ 514/311

FOREIGN PATENT DOCUMENTS

| WO | | 97/45115 | 12/1997 |
|----|----|----------|---------|
| WO | WO 97/45423 | | 12/1997 |

* cited by examiner

*Primary Examiner*—James O. Wilson
*Assistant Examiner*—Zachary Tucker
(74) *Attorney, Agent, or Firm*—William M. Blackstone

(57) ABSTRACT

The present invention relates to aminomethylcarboxylic acid derivatives general formula (I), wherein Z is $(CH_2)_n$, O, S, SO, $SO_2$ or $N-R_5$; n is 0, 1 or 2; X represents 1–3 substituents independently selected from hydrogen, halogen, $(C_{1-6})$alkyloxy, $(C_{3-6})$cycloalkyloxy, $(C_{6-12})$aryloxy, $(C_{6-12})$aryl, thienyl, $SR_6$, $SOR_6$, $SO_2R_6$, $NR_6R_6$, $NHR_6$, $NH_2$, $NHCOR_6$, $NSO_2R_6$, CN, $COOR_6$ and $(C_{1-4})$alkyl, optionally substituted with halogen, $(C_{6-12})$aryl, $(C_{1-6})$alkyloxy or $(C_{6-12})$aryloxy; or 2 substituents at adjacent positions together represent a fused $(C_{5-6})$aryl group, a fused $(C_{5-6})$cycloalkyl ring or $O-(CH_2)_m-O$; m is 1 or 2; Y represents 1–3 substituents independently selected from hydrogen, halogen, $(C_{1-4})$alkyloxy, $SR_6$, $NR_6R_6$ and $(C_{1-4})$alkyl, optionally substituted with halogen; $R_1$ is $COOR_7$ or $CONR_8R_9$; $R_2$ and $R_6$ are $(C_{1-4})$alkyl; $R_3$, $R_4$ and $R_5$ are independently hydrogen or $(C_{1-4})$alkyl; $R_7$, $R_8$ and $R_9$ are independently hydrogen, $(C_{1-4})$alkyl, $(C_{6-12})$aryl or arylalkyl; or a pharmaceutically acceptable salt thereof. The invention also relates to pharmaceutical compositions comprising said derivatives, as well as to the use of these aminomethylcarboxylic acid derivatives in therapy, more specifically for the treatment of CNS disorders.

22 Claims, No Drawings

AMINOMETHYLCARBOXYLIC ACID DERIVATIVES

FIELD OF THE INVENTION

The invention relates to aminomethylcarboxylic acid derivatives, to pharmaceutical compositions containing the same, as well as to the use of these aminomethylcarboxylic acid derivatives in therapy.

BACKGROUND OF THE INVENTION

The simplest α-amino acid glycine, or aminomethylcarboxylic acid, has a number of important roles in the mammalian central nervous system (CNS). Along with γ-aminobutyric acid (GABA), it is a major post-synaptic inhibitory transmitter in the spinal cord and brainstem, acting through ligand gated ion channels. Interaction of glycine with these receptors can be antagonized by the alkaloid strychnine. These receptors are therefore referred to as 'strychnine sensitive' glycine receptors. Glycinergic neurotransmission is important in the processing and control of visual, auditory and motor signalling. Glycine is also an obligatory co-agonist along with glutamate at the N-methyl-D-aspartate (NMDA) receptor. Glycine therefore functions in excitatory transmission by modulating the actions of glutamate, the major excitatory neurotransmitter in the CNS. In addition the amino acid plays a role in the metabolism of peptides and proteins, including the exchange of one-carbon units.

Control of the availability of glycine for any of the above processes will potentially influence their function and provide means of treating a number of diseases and conditions. Apart from metabolism, one of the major processes controlling the concentrations of free glycine in the proximity of strychnine-sensitive and strychnine-insensitive glycine receptors is the functioning of selective high affinity glycine transporters. These proteins can actively limit the spread of glycine beyond the immediate environs of receptors, thus maintaining both spatial and temporal fidelity of receptor activation. Rapid sequestering of transmitter into neuronal or glial cells via the transporter will also conserve glycine for future release.

Glycine transporters have been cloned to reveal two major classes, GlyT-1 and GlyT-2. GlyT-1 is expressed throughout the brain with higher mRNA levels being detected in caudal areas and cellular localisation being predominantly glial. Three isoforms of GlyT-1, 1a, 1b and 1c, arising from differential splicing and exon usage have been identified by Kim et al. (Molecular Pharm. 1994, 45, 608–617).

GlyT-2 distribution, as indicated by immunochemistry studies, corresponds closely to that of inhibitory 'strychnine sensitive' glycine receptors, particularly in the spinal cord.

By regulating the synaptic levels of glycine, the glycine transporters GlyT-1 and GlyT-2 are expected to selectively influence the activity at NMDA receptors and at strychnine-sensitive glycine receptors, respectively.

Compounds which after the functional activity of glycine transporters may therefore result in changes in tissue glycine levels which can be useful in the treatment of a number of disease states. Such disease states include those associated with decreased or exaggerated function of NMDA receptors, namely psychosis, depression, dementia and other forms of impaired cognition, such as attention deficit disorders. NMDA receptors have further been implicated in conditions arising from neuronal cell death and neurodegeneration such as, for example, stroke (head trauma), Alzheimer's disease, Parkinson's disease and Huntington's disease. Enhanced inhibitory glycinergic transmission resulting from inhibition of GlyT-2 or GlyT-1 activity may be useful in the treatment of muscle hyperactivity associated with spasticity, myoclonus and epilepsy. Compounds elevating spinal glycine may also possess analgesic properties.

Aminomethylcarboxylic acid derivatives, wherein the amino group carries an ethyl or a propyl-group which is substituted by two or three aryl and/or aryloxy groups, are disclosed in WO 97/45115 (TROPHIX PHARM. INC.) as compounds useful in the treatment of the neurological and neuropsychiatric disorders discussed above. Structurally related aminomethylcarboxylic acid derivatives, wherein the aminogroup is part of a cyclic amine which is substituted at a single position with (a substituent containing) two aryl or cycloalkyl groups, are disclosed in WO 97/45423 (TROPHIX PHARM. INC.) as having similar activity.

There exists a need for additional compounds suitable for the treatment of psychiatric and neurological disorders, especially for compounds having a selective pharmacological profile.

SUMMARY OF THE INVENTION

To that aim the present invention provides in a first aspect aminomethylcarboxylic acid derivatives having the general formula I

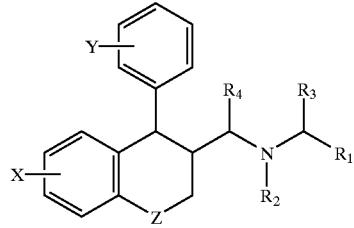

Formula I wherein
Z is $(CH_2)_n$, O, S, SO, $SO_2$ or N—$R_5$;
n is 0, 1 or 2;
X represents 1–3 substituents independently selected from hydrogen, halogen, $(C_{1-6})$alkyloxy, $(C_{3-6})$cycloalkyloxy, $(C_{6-12})$aryloxy, $(C_{6-12})$aryl, thienyl, $SR_6$, $SOR_6$, $SO_2R_6$, $NR_6R_6$, $NHR_6$, $NH_2$, $NHCOR_6$, $NHSO_2R_6$, CN, $COOR_6$ and $(C_{1-4})$alkyl, optionally substituted with halogen, $(C_{6-12})$aryl, $(C_{1-6})$alkyloxy or $(C_{6-12})$aryloxy; or 2 substituents at adjacent positions together represent a fused $(C_{5-6})$aryl group, a fused $(C_{5-6})$cycloalkyl ring or O—$(CH_2)_m$—O; m is 1 or 2;
Y represents 1–3 substituents independently selected from hydrogen, halogen, $(C_{1-4})$alkyloxy, $SR_6$, $NR_6R_6$ and $(C_{1-4})$alkyl, optionally substituted with halogen;
$R_1$ is $COOR_7$ or $CONR_8R_9$;
$R_2$ and $R_6$ are $(C_{1-4})$alkyl;
$R_3$, $R_4$ and $R_5$ are independently hydrogen or $(C_{1-4})$alkyl;
$R_7$, $R_8$ and $R_9$ are independently hydrogen, $(C_{1-4})$alkyl, $(C_{6-12})$aryl or arylalkyl;
or a pharmaceutically acceptable salt thereof.

The term $(C_{1-4})$alkyl, as used in the definition of formula I, means a branched or unbranched alkyl group having 1–4 carbon atoms, for example, butyl, isobutyl, tertiary butyl, propyl, isopropyl, ethyl and methyl.

In the term $(C_{1-6})$alkyloxy, $(C_{1-6})$alkyl means a branched or an unbranched alkyl group having 1–6carbon atoms, for example hexyl, pentyl, neopentyl (2,2-dimethylpropyl) and the meanings given above for $(C_{1-4})$alkyl. The $(C_{1-6})$ alkyloxy group may be substituted with halogen, $(C_{3-6})$ cycloalkyl or $(C_{1-4})$alkyloxy. Examples of such substituted $(C_{1-6})$alkyloxy groups are trifluoromethyloxy and cyclopropylmethyloxy.

The term $(C_{3-6})$cycloalkyl means a cyclic alkyl group having 3–6 carbon atoms, for example cyclopropyl, cyclobutyl, cyclopentyl or cyclohexyl.

The term halogen means F, Cl, Br, or I. When halogen is a substituent at an alkyl group, F is preferred. A preferred halogen substituted alkyl group is trifluoromethyl.

In the term $(C_{6-12})$aryloxy, as used in the definition of formula I, $(C_{6-12})$aryl means an aromatic group having 6–12 carbon atoms for example phenyl, naphthyl or biphenyl. These aromatic groups may be substituted with halogen, or with $(C_{1-4})$alkyl or $(C_{1-4})$alkyloxy, wherein $(C_{1-4})$alkyl has the previously given meaning and may be substituted with halogen or $(C_{1-4})$alkyloxy.

The term arylalkyl, as used in the definition of Formula I, means a $(C_{1-4})$alkyl group which is substituted with a $(C_{6-12})$aryl group, for example, benzyl.

In the definition of formula I, X can represent a fused $(C_{5-6})$aryl group, which means that X is a 5 or 6-membered aromatic ring fused to the benzene ring to which X is attached to form a $(C_{11-12})$aromatic ring system, for example a naphthalene or an indene ring. X can also represent a fused $(C_{5-6})$cycloalkyl ring, which means that X is a 5- or 6-membered saturated ring fused to the benzene ring to which X is attached to form a tetrahydronaphthalene or an indan ring system. X may further represent $O—(CH_2)_m—O$, wherein m is 1 or 2, which is fused to the benzene ring to which X is attached to form a 1,3-benzodioxole (m=1) or a 1,4-benzodioxan (m=2) ring system.

The meaning of $R_1$ in formula I is exemplified by the groups $COOR_7$ and $CONR_8R_9$. In addition $R_1$ may be any other group from which the free acid ($R_1$=COOH) can be generated (in vivo). Such alternative acid precursors or prodrugs, such as further ester or amide derivatives, are known in the art, and are within the scope of the present invention.

The invention includes as specific examples of aminomethylcarboxylic acid derivatives of formula I the (4-phenyl-3,4-dihydro-2H-1-benzothiopyran-3-ylmethyl) aminomethylcarboxylic acid derivatives, wherein Z=S; and the (4-phenyl-3,4-dihydro-2H-1-benzopyran-3-ylmethyl) aminomethylcarboxylic acid derivatives, wherein Z=O.

Preferred aminomethylcarboxylic acid derivatives of the invention correspond to compounds of formula I wherein Z is $(CH_2)_n$ and n is 1, and wherein $R_1$–$R_4$, X and Y have the previously given meanings. These compounds are (1-phenyl-1,2,3,4-tetrahydronaphthalen-2-ylmethyl) aminomethylcarboxylic acid derivatives, of which the derivatives wherein $R_2$ is methyl and $R_3$ and $R_4$ are hydrogen, are further preferred. Particularly preferred are the derivatives wherein in addition $R_1$ is $COOR_7$. Most preferred are the compounds of formula 1 wherein Z is $(CH_2)_n$, n is 1, $R_1$ is COOH, $R_2$ is methyl, $R_3$ and $R_4$ are hydrogen, and pharmaceutically acceptable salts thereof. Ring substituent(s) X, when present, may be in any one and in up to three of the available positions. Specific examples of single ring substituents X includes 6-methoxy, 6-ethoxy, 6-isopropyloxy, 6-phenoxy, 6-cyclohexyloxy, 6-cyano, 6-carboxylate, 6-trifluoromethyl, 6-trifluoromethoxy, 5-fluoro, 7-fluoro and 6-methyl. Substituent Y at the phenyl ring, when present, may be in any one and in up to three of the available positions. Specific examples of single phenyl substituents Y include 3-fluoro and 4-fluoro. An example of multiple substituents include 3,4-difluoro.

The compounds of formula I and their salts contain at least two centres of chirality, i.e. at the two adjacent positions of the Z-containing saturated ring where the phenyl group and the $CHR_4$—$NR_2$—$CHR_3R_1$ group are attached, and exist therefore as stereoisomers.

The present invention includes the aforementioned stereoisomers within its scope and each of the individual cis and trans isomers, enantiomers and diastereomers of the compounds of formula I and their salts, substantially free, i.e. associated with less than 5%, preferably less than 2%, in particular less than 1% of the other enantiomer, and mixtures of such stereoisomers in any proportions including the racemic mixtures containing substantially equal amounts of the two enantiomers.

Preferred are the aminomethylcarboxylic acid derivatives of formula I wherein the phenyl group and the $CHR_4$—$NR_2$—$CHR_3R_1$ group occur in the cis-configuration.

The compounds of the invention can be used in the treatment of schizophrenia, depression, dementia and other forms of impaired cognition, for the treatment or prevention of neurodegeneration following stroke or head trauma, for the treatment of neurodegenerative diseases like Alzheimer's-, Parkinson's- and Huntington's disease, for the treatment of muscle hyperactivity associated with spasticity, myoclonus and epilepsy, for the treatment of prevention of pain, mood disorders or learning disorders.

The invention provides in a further aspect pharmaceutical compositions comprising an aminomethylcarboxylic acid derivative having general formula I, of a pharmaceutically acceptable salt thereof, in admixture with pharmaceutically acceptable auxiliaries.

DETAILED DESCRIPTION OF THE INVENTION

Formula II

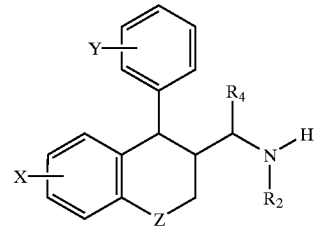

Compounds of general formula (I) may be prepared by the reaction of a compound of formula (II) wherein X, Y, Z, $R_2$ and $R_4$ have the previously defined meanings, with a compound of formula L—$CHR_1R_3$, wherein $R_1$ is $COOR_7$ or $CONR_8R_9$, $R_7$–$R_9$ and $R_3$ are as defined previously, and L is a suitable leaving group, such as for example halogen, preferably bromo. The reaction is typically carried out in the presence of a suitable solvent such as N,N-dimethylformamide and an acid scavenger such as potassium or cesium carbonate at elevated temperatures, for example at 80° C. Compounds of formula (I) wherein $R_1$ is carboxylate $COOR_7$ wherein $R_7$ is hydrogen, may be conveniently prepared by hydrolysis of the corresponding esters $COOR_7$, wherein $R_7$ is $(C_{1-4})$alkyl, $(C_{6-12})$aryl or arylalkyl, using standard conditions for ester hydrolysis, for example, by heating the aforementioned esters in a mixture of aqueous potassium hydroxide in ethanol at reflux temperature, or by catalytic hydrogenation of, for example, benzyl esters. Compounds of formula (I), wherein $R_1$ is carboxamide CONR$_8$R$_9$, wherein R$_8$ and R$_9$ are (C$_{1-4}$)alkyl may also be prepared by reaction of the aforementioned carboxylic acids with amines HNR$_8$R$_9$ using standard conditions for amide formation, for example, by reaction of the carboxylic acid with 1-(3-dimethylaminopropyl)-3-ethylcarbodiimide hydrochloride (EDC) in the presence of a tertiary amine in N,N-dimethylformamide. Alternatively they can be made by, for example by the reaction of the aforementioned carboxylic acids with thionyl chloride or oxalylchloride in methylene chloride containing a catalytic amount of N,N-dimethylformamide followed by reaction of the resulting acid chlorides with amines HNR$_8$R$_9$ in the presence of a tertiary amine acid scavenger in methylene chloride at room temperature.

Compounds of formula (II) wherein the phenyl group and the CHR$_4$—NHR$_2$ group occur in the trans configuration can be prepared from the appropriately substituted 1-phenyl-1,2,3,4-tetrahydro-2-naphthoic acids by methods well known in the art. The aforementioned 1-phenyl-1,2,3,4-tetrahydro-2-naphthoic acids, prepared by the method described in *J.Chem.Soc.*, 1936, 596–599, can, for example, react to form the corresponding acyl halides or anhydrides using standard methods. These in turn, upon reaction with amines R$_2$NH$_2$ followed by reduction of the resulting amides provide the desired compounds (II). For the reduction of the amides, sodium borohydride in the presence of certain catalysts, borane, or lithium aluminium hydride in a non-protic solvent such as diethyl-ether or tetrahydrofuran can be used.

Compounds of formula (II) wherein the phenyl group and the CHR$_4$—NHR$_2$ group occur in the cis configuration are obtained by reaction of compounds of formula (III) with hydrogen in the presence of a palladium on carbon catalyst in ethanol containing aqueous hydrochloric acid. Typically the reaction occurs in the temperature range 0–50° C. and at a pressure ranging from 1 to 4 atmospheres. Alternatively, debenzylation can be achieved by treating compounds of formula (III) with (1-chloroethyl)chloroformate in dichloromethane at reflux temperature followed by heating in the presence of methyl alcohol.

formula III

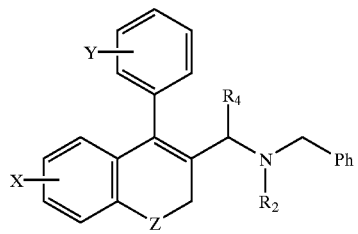

Compounds of formula (III) may conveniently be prepared by dehydration of a compound of formula (IV) using standard conditions, for example using trifluoroacetic acid at room temperature.

formula IV

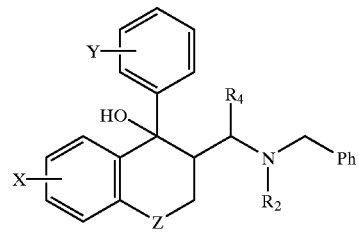

Compounds of formula (IV) may be prepared by reaction of an appropriate aryl organometallic reagent, such as a Grignard or lithium reagent derived from Aryl-L, wherein Aryl represents a phenyl group substituted with Y, which has the meaning as previously defined, and wherein L is a halogen atom such as bromo or chloro, with compounds of formula (V). The reaction is typically carried out in the presence of an apolar, aprotic solvent such as for example diethyl ether at a temperature in the range −10 to +20° C.

formula V

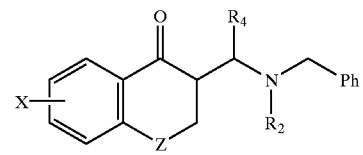

Compounds of formula (V) are obtained by reaction of compounds of formula (VI) with the appropriate aldehyde HCO—R$_4$ and a compound of formula NHR$_2$CH$_2$C$_6$H$_5$ in ethanol containing aqueous hydrochloric acid at reflux.

formula VI

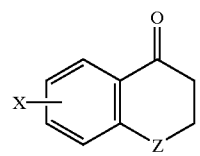

Compounds of formula (VI) are commercially available or are prepared by methods described in the literature. Such methods are, for example, described in Comprehensive Organic Transformations (by Richard C. Larock, 1989, VCH). For example, the compound of formula VI wherein X is 6-fluoro and Z is methylene may be prepared by cyclisation of 4-(3-fluorophenyl)butyric acid using an acid catalyst such as polyphosphoric acid. The latter compound can be conveniently prepared by reaction of 3-fluorobenzaldehyde with methyl acrylate in the presence of potassium cyanide in N,N-dimethylformamide, at 45° C. followed by reduction of the resultant oxobutanoate using hydrazine hydrate and potassium hydroxide in ethanol glycol at reflux temperature. Similarly the compound wherein X is 6-thiomethyl and Z is methylene can be prepared from the commercially available 6-methoxy analogue by the method described in *Chem. Pharm. Bull.*, 1984, 32, 130.

Compounds wherein X is (C$_{1-6}$)alkyloxy, wherein (C$_{1-6}$) alkyloxy has the meaning as previously defined, can be prepared from the 6-methoxy analogue by treatment with hydrogen bromide in acetic acid followed by reaction of the resulting phenol with an appropriate alkyl halide, typically an alkyl bromide or alkyl iodide in dimethylformamide in the presence of a suitable acid scavenger such as potassium or cesium carbonate at elevated temperatures. Alternatively, the required ethers can be prepared by reaction of the phenol with an alcohol according to Mitsunobo's conditions which are known to those skilled in the art.

Compounds wherein X is ($C_{6-12}$)aryloxy, wherein ($C_{6-12}$) aryloxy is defined as above, can be prepared from the aforementioned phenol using the methods described in *Chem. Pharm.Bull.* 1978, 26, 2475–2482. Said phenol derivatives can likewise be converted with triflic anhydride to the corresponding triflate derivative, the trifate group of which can be converted, using methods known to the skilled person, to an amino group.

Compounds of formula (VI) wherein Z is oxygen can be prepared as described in *J.Chem.Soc.*, 1954, 4299–4303; those wherein Z is S can be synthesized as indicated in *J.Am.Chem.Soc.*, 1954, 76, 5065–5069.

The skilled person will be aware of numerous general synthetic methods that allow the conversion of a certain group X in a compound according to one of the Formulas I–VI to another group X according to the definition of X. For example, a compound according to formula III; wherein X is a 6-bromo group, can be sequentially converted to a methoxycarbonyl group (X=$COOR_6$, wherein $R_6$ is methyl) and a cyano group.

The compounds of this invention possess at least two chiral carbon atoms, and can therefore be obtained as pure stereoisomers, or as a mixture of stereoisomers. Methods for asymmetric synthesis whereby the pure stereoisomers are obtained are well known in the art, e.g. synthesis with chiral induction, enantioselective enzymatic ester hydrolysis, crystallization of salts which are obtained from optically active acids and the racemic mixture, separation of stereoisomers or enantiomers using chromatography on chiral media, or on straight phase or reversed phase chromatography media. Such methods are for example described in *Chirality in Industry* (edited by A. N. Collins, G. N. Sheldrake and J. Crosby, 1992; John Wiley).

Pharmaceutically acceptable salts of the compounds of formula I may be obtained by treating the free base of the compounds according to formula I with a mineral acid such as dihydrochloric acid, phosphoric acid, sulphuric acid, preferably hydrochloric acid, or with an organic acid such as for example ascorbic acid, citric acid, tartaric acid, lactic acid, maleic acid, malonic acid, fumaric acid, glycolic acid, succinic acid, propionic acid, acetic acid, methanesulphonic acid and the like. Pharmaceutically acceptable salts of compounds of formula I wherein $R_1$ is $COOR_7$ and $R_7$ is hydrogen, may be obtained by treating the acid or zwitterionic form of those compounds with an organic base or a mineral base, for example sodium, potassium or lithium hydroxide.

The compounds of the invention may be administered for humans in a dosage of 0.001–50 mg per kg body weight, preferably in a dosage of 0.01–20 mg per kg body weight.

The pharmaceutical compositions for use according to the invention comprise an aminomethylcarboxylic acid derivative having formula I or a pharmaceutically acceptable salt thereof in admixture with pharmaceutically acceptable auxiliaries, and optionally other therapeutic agents. The term "acceptable" means being compatible with the other ingredients of the composition and not deleterious to the recipients thereof. The compositions can be prepared in accordance with standard techniques such as for example are described in the standard reference, Gennaro et al., Remington's Pharmaceutical Sciences, (18th ed., Mack Publishing Company, 1990, see especially Part 8: Pharmaceutical Preparations and Their Manufacture). Compositions include e.g. those suitable for oral, sublingual, intranasal, subcutaneous, intravenous, intramuscular, local, or rectal administration, and the like, all in unit dosage forms for administration.

For oral administration, the active ingredient may be presented as discrete units, such as tablets, capsules, powders, granulates, solutions, and suspensions.

For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

The invention further includes a pharmaceutical composition, as hereinbefore described, in combination with packaging material suitable for said composition, said packaging material including instructions for the use of the composition for the use as hereinbefore described.

EXAMPLES

The invention is illustrated by the following examples.
General:
All mass spectrometry was carried out on either a PE SCIEX API 150EX or a PE SCIEX API 365 machine. Melting points are uncorrected and were determined using a Leica Galen III instrument. Optical rotations were determined on a Shimadzu Graphicord UV-Visible recording spectrophotometer.

Example 1

(see Scheme for Process 1).
Lithium cis-N-methyl-N-(6-fluoro-1-phenyl-1,2,3,4-tetrahydronaphthalen-2-ylmethyl) aminomethylcarboxylate.
Step A: Methyl-4-(3-fluorophenyl)-4-oxobutanoate To a stirred suspension of potassium cyanide (3.25 g) in N,N-dimethylformamide (30 cm³), being maintained at a temperature of 45° C., was added 3-fluorobenzaldehyde (25.0 g). Ethyl acrylate (18.46 cm³) was then added and the resultant mixture was stirred at 40° C. for 2 h. Water (200 cm³) was added and the aqueous mixture was extracted with diethyl ether (2×125 cm³). The organic extracts were washed with water (100 cm³) and saturated aqueous sodium chloride solution (100 cm³) before being dried ($Na_2SO_4$) and the solvent was removed under reduced pressure to yield the title compound (25.27 g) as a yellow oil.

Scheme for Process 1

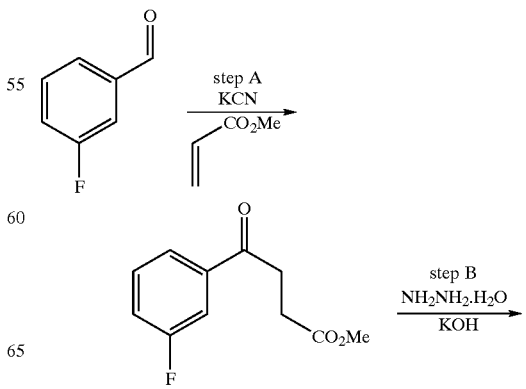

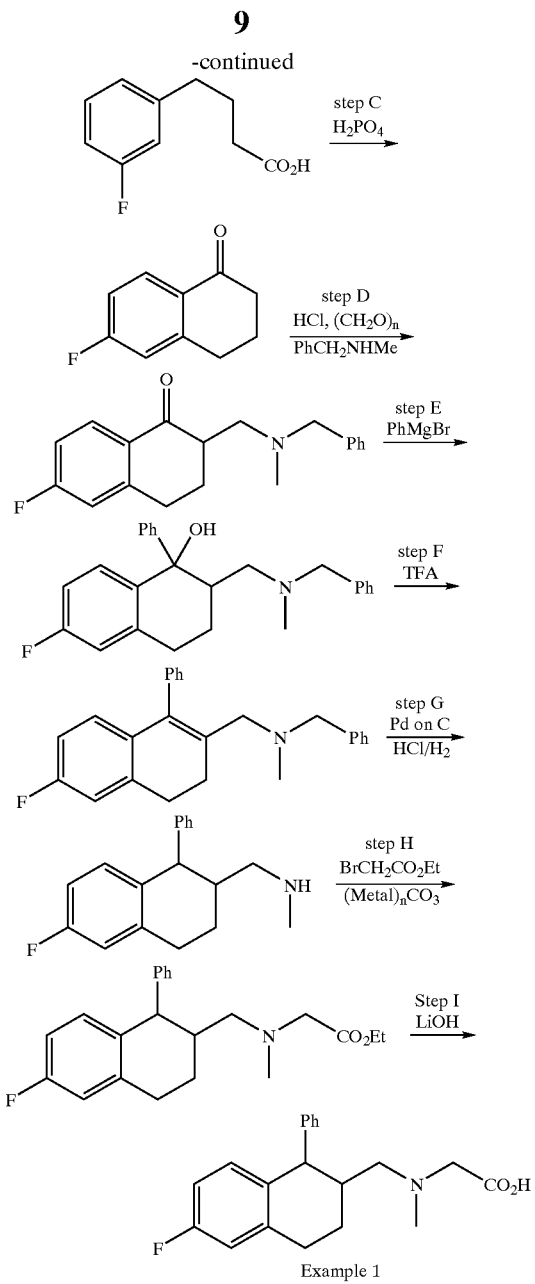

Example 1

Step B: 4-(3-Fluorophenyl)butanoic acid

Methyl-4-(3-fluorophenyl)-4-oxobutanoate (25.27 g), hydrazine hydrate (24.29 cm³) and potassium hydroxide pellets (20.50 g) were dissolved in ethylene glycol (150 cm³) and the mixture was heated at reflux for 1.25 h. The excess hydrazine hydrate was distilled off until the temperature at the still-head reached 160° C. The reaction mixture was then cooled, diluted with water (400 cm³) and the resultant aqueous mass was washed with diethyl ether (2×150 cm³) and then acidified with hydrochloric acid (5 M, 150 cm³). The acidic mixture was then extracted with diethyl ether (2×150 cm³) and the combined extracts were dried (Na₂SO₄) and the solvent was removed under reduced pressure to provide the title compound (15.51 g) as a dark oil.

Step C: 6-Fluoro-3,4-dihydro-2H-naphthalene-1-one

A mixture of 4-(3-fluorophenyl)butanoic acid (10 g) and polyphosphoric acid (100 g) was heated to 70° C. with stirring for 2 h. The reaction mixture was cooled and water was carefully added (400 cm³). The aqueous mixture was extracted with diethyl ether (3×75 cm³) and the combined extracts were washed sequentially with aqueous potassium hydroxide solution (1 M, 75 cm³), water (75 cm³) and saturated aqueous sodium chloride solution (75 cm³). The combined organic extracts were dried (Na₂SO₄), and the solvent was distilled off under reduced pressure. The crude product (6.58 g) was purified by column chromatography [silica, eluting with petroleum ether (b. p. 40–60° C.)-ethyl acetate (20:1)] to afford the title compound (6.36 g).

Step D: 2-(N-Benzylmethylamino)methyl-6-fluoro-3,4-dihydro-2H-naphthalene-1-one hydrochloride To an ice-cooled solution of N-benzylmethylamine (5.67 cm³) in ethyl alcohol (60 cm³) was added hydrochloric acid (5 M, 10 cm³). 6-Fluoro-3,4-dihydro-2H-naphthalene-1-one (6.00 g) and paraformaldehyde (1.32 g) were then added and the resulting mixture was stirred and heated to reflux for 4 h. Upon cooling, the alcohol was removed under reduced pressure and water (100 cm³) was added. The remaining tetralone was extracted into diethyl ether (100 cm³) and the aqueous mixture was then extracted further with dichloromethane (2×100 cm³). The combined extracts were dried (Na₂SO₄) and concentrated under reduced pressure. Trituration with diethyl ether and filtration provided the title compound (3.18 g) as a white solid.

Step E: 2-(N-Benzylmethylamino)methyl-6-fluoro-1-phenyl-1,2,3,4-tetrahydronaphthalene-1-ol Phenylmagnesium bromide (3 M solution in diethyl ether, 9 cm³) was added to dry diethyl ether (20 cm³) under nitrogen with stirring. This was then cooled to below 0° C. (salt-ice bath) and 2-(N-benzylmethylamino)methyl-6-fluoro-3,4-dihydro-2H-naphthalene-1-one hydrochloride was added in small portions at such a rate as to maintain the temperature below 0° C. (approx. 15 mins). The reaction mixture was stirred for a further 1 h at 0° C. and then poured onto ice. Water (100 cm³) and diethyl ether (100 cm³) were added and the aqueous layer was separated and extracted with further diethyl ether (100 cm³). The combined ether layers were extracted with hydrochloric acid (5 M, 3×50 cm³). The acidic extracts were basified (K₂CO₃) and re-extracted with dichloromethane (3×75 cm³). The combined extracts were dried (Na₂SO₄) and the solvent was removed under reduced pressure to provide the title compound (1.55 g) as a brown oil which solidified on standing.

Step F: 2-(N-Benzylmethylamino)methyl-6-fluoro-1-phenyl-3,4-dihydronaphthalene

Trifluoroacetic acid (10 cm³) was added to 2-(N-benzylmethylamino)methyl-6-fluoro-1-phenyl-1,2,3,4-tetrahydronaphthalene-1-ol (1.5 g) and the resulting solution was stirred at room temperature for 2 h. The excess trifluoroacetic acid was removed under reduced pressure and the resultant brown oil was taken up into petroleum ether (b. p. 40–60° C.) and passed through a short column [basic alumina, eluting with petroleum ether (b. p. 40–60° C.)-ethyl acetate (20:1)]. The fractions containing the product were combined and the solvent removed under reduced pressure to afford the title compound (0.97 g).

Step G: cis-6-Fluoro-2-methylaminomethyl-1-phenyl-1,2,3,4-tetrahydronaphthalene hydrochloride To a mixture of 2-(N-benzylmethylamino)methyl-6-fluoro-1-phenyl-3,4-dihydronaphthalene (0.95 g) in ethyl alcohol (50 cm³) and hydrochloric acid (5 M, 1 cm³) was added palladium on charcoal (5%, 0.25 g). The resultant mixture was stirred under an atmosphere of hydrogen at a pressure of 2 atm at room temperature for 60 h. The catalyst was removed by filtration through a pad of Dicalite® and the solvent was evaporated under reduced pressure to provide the title compound (0.75 g) as a white solid.

Step H: Ethyl cis-N-methyl-N-(6-fluoro-1-phenyl-1,2,3,4-tetrahydronaphthalen-2-ylmethyl) aminomethylcarboxylate To a mixture of cis-6-fluoro-2-methylaminomethyl-1-phenyl-1,2,3,4-tetrahydronaphthalene hydrochloride (0.74 g), cesium carbonate (2.36 g) and N,N-dimethylformamide (15 cm$^3$) was added ethyl bromoacetate (0.29 cm$^3$) and the resulting mixture was stirred and heated at 80° C. for 4 h. The reaction was allowed to cool to room temperature and water (100 cm$^3$) was added before the mixture was extracted with diethyl ether (2×100 cm$^3$). The combined organic extracts were washed with water (100 cm$^3$), dried (Na$_2$SO$_4$) and the solvent was evaporated under reduced pressure. The crude product (0.95 g) was purified by column chromatography [silica, eluting with petroleum ether (b. p. 40–60° C.)-ethyl acetate (5:1)] to yield the title compound (0.73 g). Positive ion ESI (M+H)$^+$ 356.2.

Step I: Lithium cis-N-methyl-N-(6-fluoro-1-phenyl-1,2,3,4-tetrahydronaphthalen-2-ylmethyl) aminomethylcarboxylate To a solution of ethyl cis-N-methyl-N-(6-fluoro-1-phenyl-1,2,3,4-tetrahydronaphthalen-2-ylmethyl) aminomethylcarboxylate (0.1 g) in ethyl alcohol (0.5 cm$^3$) was added a solution of aqueous lithium hydroxide (2 M, 0.15 cm$^3$). The reaction mixture was heated to 80° C. with stirring for 3 h. Upon cooling to room temperature, the solvent was removed under reduced pressure to afford the title compound (90 mg) as a white solid; m. p. 133–136° C.; positive ion ESI (M+H)$^+$ 328.4.

The following compounds (Examples 2–22) were prepared in a similar manner (using the process steps of Scheme 1) from the appropriate α-tetralones:

Example 2
Lithium cis-N-methyl-N-[6-fluoro-1-(4-fluorophenyl)-1,2,3,4-tetrahydronaphthalen-2-ylmethyl] aminomethylcarboxylate; m. p. 141–145° C.; positive ion ESI (M+H)$^+$ 346.2.

Example 3
Lithium cis-N-methyl-N-[1-(4-fluorophenyl)-1,2,3,4-tetrahydronaphthalen-2-ylmethyl] aminomethylcarboxylate; m. p. 177–183° C.; negative ion ESI (M–H)$^-$ 326.4.

Example 4
Lithium cis-N-methyl-N-(6-methoxy-1-phenyl-1,2,3,4-tetrahydronaphthalen-2-ylmethyl) aminomethylcarboxylate; positive ion ESI (M–H)$^+$ 340.3.

Example 5
Lithium cis-N-methyl-N-[1-(4-fluorophenyl)-6-methoxy-1,2,3,4-tetrahydronaphthalen-2-ylmethyl] aminomethylcarboxylate; m. p. 129–132° C.; positive ion ESI (M–H)$^+$ 358.2.

Example 6
Lithium cis-N-methyl-N-(7-methoxy-1-phenyl-1,2,3,4-tetrahydronaphthalen-2-ylmethyl) aminomethylcarboxylate; positive ion ESI (M+H)$^+$ 340.3.

Example 7
Lithium cis-N-methyl-N-(1-phenyl-6-trifluoromethyl-1,2,3,4-tetrahydronaphthalen-2-ylmethyl) aminomethylcarboxylate; m. p. 131–137° C.; positive ion ESI (M+H)$^+$ 378.2.

Example 8
Lithium cis-N-methyl-N-[1-(4-fluorophenyl)-6-trifluoromethyl-1,2,3,4-tetrahydronaphthalen-2-ylmethyl] aminomethylcarboxylate; m. p. 137–142° C.; positive ion ESI (M+H)$^+$ 396.2.

Example 9
Lithium cis-N-methyl-N-[1-(2,4-difluorophenyl)-6-methoxy-1,2,3,4-tetrahydronaphthalen-2-ylmethyl] aminomethylcarboxylate; positive ion ESI (M+H)$^+$ 376.4.

Example 10
Lithium cis-N-methyl-N-[1-(3,4-difluorophenyl)-6-methoxy-1,2,3,4-tetrahydronaphthalen-2-ylmethyl] aminomethylcarboxylate; positive ion ESI (M+H)$^+$ 376.4.

Example 11
Lithium cis-N-methyl-N-[6-ethoxy-1-(4-fluorophenyl)-1,2,3,4-tetrahydronaphthalen-2-ylmethyl] aminomethylcarboxylate; positive ion ESI (M+H)$^+$ 372.2.

Example 12
Lithium cis-N-methyl-N-(5-fluoro-1-phenyl-1,2,3,4-tetrahydronaphthalen-2-ylmethyl) aminomethylcarboxylate; m. p. 159–161° C.; positive ion ESI (M+H)$^+$ 328.4.

Example 13
Lithium cis-N-methyl-N-[7-fluoro-1-(4-fluorophenyl)-1,2,3,4-tetrahydronaphthalen-2-ylmethyl] aminomethylcarboxylate; positive ion ESI (M+H)$^+$ 346.2.

Example 14
Lithium cis-N-methyl-N-(7-fluoro-1-phenyl-1,2,3,4-tetrahydronaphthalen-2-ylmethyl) aminomethylcarboxylate; m. p. 137–158° C.; positive ion ESI (M+H)$^+$ 328.2.

Example 15
Lithium cis-N-methyl-N-(1-phenyl-6-trifluoromethoxy-1,2,3,4-tetrahydronaphthalen-2-ylmethyl) aminomethylcarboxylate; m. p. 127–129° C.; positive ion ESI (M+H)$^+$ 394.2.

Example 16
Lithium cis-N-methyl-N-(6-ethoxy-1-phenyl-1,2,3,4-tetrahydronaphthalen-2-ylmethyl) aminomethylcarboxylate; m. p. 238–249° C.

Example 17
Lithium cis-N-methyl-N-(6-phenoxy-1-phenyl-1,2,3,4-tetrahydronaphthalen-2-ylmethyl) aminomethylcarboxylate; m. p. 191–200° C.

Example 18
Lithium cis-N-methyl-N-(6-isopropyloxy-1-phenyl-1,2,3,4-tetrahydronaphthalen-2-ylmethyl) aminomethylcarboxylate; positive ion ESI (M+H)$^+$ 374.4.

Example 19
Lithium cis-N-methyl-N-[6-methoxy-1-(4-methoxyphenyl)-1,2,3,4-tetrahydronaphthalen-2-ylmethyl] aminomethylcarboxylate; m. p. 148–150° C.; positive ion ESI (M+H)$^+$ 370.4.

Example 20
cis-N-Methyl-N-[6-methoxy-1-(3-methylphenyl)-1,2,3,4-tetrahydronaphthalen-2-ylmethyl] aminomethylcarboxylic acid trifluoroacetic acid salt; m. p. 96–106° C.; positive ion ESI (M+H)$^+$ 354.4.

Example 21
Lithium cis-N-methyl-N-(4-phenyl-3,4-dihydro-2H-1-benzothiopyran-3-ylmethyl) aminomethylcarboxylate. Prepared as a brown froth, according to the generic protocol from commercially available thiochroman-4-one; positive ion ESI (M+H)$^+$ 328.0.

Example 22
Lithium cis-N-methyl-N-(4-phenyl-3,4-dihydro-2H-1-benzopyran-3-ylmethyl) aminomethylcarboxylate; prepared from 4-chromanone; m. p. 207–210° C.; positive ion ESI (M+H)$^+$ 312.4.

Example 23
Lithium cis-N-methyl-N-(6-methyl-1-phenyl-1,2,3,4-tetrahydronaphthalen-2-ylmethyl) aminomethylcarboxylate
A: 4-(3-Methylphenyl)-4-oxobutanoic acid N,N-Dimethylamidosuccinic acid (14.5 g) was dissolved in anhydrous tetrahydrofuran (400 cm$^3$) and stirred at 0° C. To this was added a solution of m-tolyl-magnesium chloride in tetrahydrofuran (1 M, 200 cm$^3$) over a period of approximately 2.5 h. Once the addition was complete the reaction mixture was stirred for a further 2 h. Saturated aqueous ammonium chloride (200 cm$^3$) was added and most of the tetrahydrofuran was distilled off under reduced pressure before the residue was treated with ether (100 cm$^3$). After acidification with hydrochloric acid (5 M) the aqueous component was extracted with ethyl acetate (2×100 cm$^3$), dried (Na$_2$SO$_4$) and the solvent was removed under reduced pressure to provide the title compound (8.8 g).
B: Starting from 4-(3-methylphenyl)-4-oxobutanoic acid and using procedures similar to those described in the Scheme 1 for Process 1, the title compound was obtained; m. p. 135–138° C.; positive ion ESI (M+H)$^+$ 324.2.

Example 24
Lithium cis-N-methyl-N-(1-phenyl-1,2,3,4,5,6,7,8-octahydrophenanthrenemethyl) aminomethylcarboxylate
A: 4-(1-Naphthyl)butenoic acid To a mixture of 3-triphenylphosphorylpropionic acid chloride (12.40 g) and 1-naphthaldehyde in dry tetrahydrofuran (30 cm$^3$) at 0° C. under an atmosphere of nitrogen was added a solution of potassium tert-butoxide (7.54 g) in tetrahydrofuran (30 cm$^3$) over a period of 1 h. The reaction was allowed to warm to room temperature and stirred for a further 12 h before it was quenched with water (40 cm$^3$) and extracted with diethyl ether (2×40 cm$^3$). The aqueous portion was acidified with hydrochloric acid (5 M) and extracted into dichloromethane (3×40 cm$^3$). The organic extracts were dried (Na$_2$SO$_4$) and the solvent was removed under reduced pressure to give a brown oil that crystallised on standing. The product was re-crystallised from aqueous ethyl alcohol to afford the title compound (3.96 g).
B: 4-(1-Naphthyl)butanoic acid To a solution of 4-(1-naphthyl)butenoic acid (3.96 g) in ethyl alcohol (45 cm$^3$) was added palladium on carbon (10%, 400 mg). The mixture was stirred under hydrogen (approx. 2 atm) for 3 h. The catalyst was then removed by filtration through a pad of Dicalite® and the solvent was removed under reduced pressure to yield the title compound (3.59 g).
C: 3,4,-Dihydro-2H-phenanthren-1-one To 4-(1-naphthyl)butanoic acid (3.52 g) was added polyphosphoric acid (35.0 g) and the mixture was stirred at 40° C. for 20 h. The reaction was then diluted with water (200 cm$^3$) and extracted with dichloromethane (3×100 cm$^3$). The organic extracts were washed with water, aqueous sodium hydrogen carbonate solution (0.5 M) and then saturated aqueous sodium chloride solution. It was then dried (Na$_2$SO$_4$) and the solvent was removed under reduced pressure to afford the title compound as an oil that solidified on standing (3.09 g).
D: 2-(N-Benzylmethylamino)methyl-3,4-dihydro-2H-phenanthren-1-one hydrochloride A mixture of 3,4-dihydro-2H-phenanthren-1-one (3.09 g), benzylmethylamine (2.51 g), paraformaldehyde (0.8 g), hydrochloric acid (5 M, 4.76 cm$^3$) and ethyl alcohol (60 cm$^3$) was heated to reflux for 48 h. It was then allowed to cool to room temperature and the alcohol was removed under reduced pressure. Water (100 cm$^3$) was added and the remaining phenanthren-1-one was extracted into diethyl ether (2×100 cm$^3$). The aqueous layer was further extracted with dichloromethane (2×100 cm$^3$) and the combined dichloromethane extracts were dried (Na$_2$SO$_4$) and concentrated under reduced pressure to afford the title compound as a pink solid (3.5 g).
E: Lithium cis-N-methyl-N-(1-phenyl-1,2,3,4,5,6,7,8-octahydrophenanthrenemethyl) aminomethylcarboxylate (0.20 g) was prepared from 2-(N-benzylmethylamino)methyl-3,4-dihydro-2H-phenanthren-1-one hydrochloride according to procedures similar to those set in Scheme for Process 1. The only difference being that during the hydrogenation step one of the aromatic rings became saturated; m. p. 164–166° C.; positive ion ESI (M+H)$^+$ 364.4.

Example 25
cis-N-Methyl-N-(1-phenyl-1,2,3,4-tetrahydronaphthalen-2-ylmethyl) aminomethylcarboxylic acid hydrochloride To a solution of ethyl cis-N-methyl-N-(1-phenyl-1,2,3,4-tetrahydronaphthalen-2-ylmethyl) aminomethylcarboxylate (0.1 g, prepared using the methods described in Process 1 of Example 1) in ethyl alcohol (2 cm$^3$) was added potassium hydroxide (10 M, 0.1 cm$^3$). The reaction mixture was heated and stirred at 80° C. for 3 h. Upon cooling, the alcohol was removed under reduced pressure and water (10 cm$^3$) was added. The aqueous mixture was washed with ethyl acetate (2×10 cm$^3$), acidified with aqueous hydrochloric acid (5 M) and concentrated under reduced pressure. Crystallisation from methyl alcohol-diethyl ether provided the title compound as a white solid (0.012 g); m. p. 205–211° C. (decomp.); positive ion ESI (M+H)$^+$ 310.2.

Similarly obtained was:

Example 26
cis-N-Methyl-N-[(1-(3-fluorophenyl)-1,2,3,4-tetrahydronaphthalen-2-ylmethyl] aminomethylcarboxylic acid hydrochloride; m. p. 212–218° C.; positive ion ESI (M+H)$^+$ 328.2.

Example 27
cis-N-Methyl-N-[1-(4-trifluoromethylphenyl)-1,2,3,4-tetrahydronaphthalen-2-ylmethyl] aminomethylcarboxylic acid hydrochloride
A: 2-(N-Benzylmethylamino)methyl-1-(4-trifluoromethylphenyl)-3,4-dihydro-2H-naphthalen-1-ol To a cooled (−78° C.), stirred mixture of n-butyllithium in hexane (1.6 M, 34.7 cm$^3$) and diethyl ether (25 cm$^3$) was added 4-bromobenzotrifluoride (7.8 g). After a further 15 min, 2-(N-benzylmethylamino)methyl-3,4-dihydro-2H-naphthalen-1-one hydrochloride (prepared using methods described in Process 1) was added portion-wise. The reaction mixture was then stirred for 1 h before being allowed to warm to room temperature and then water (50 cm$^3$) was added. The organic layer was separated and washed with water (50 cm$^3$). It was then extracted with hydrochloric acid (2 M, 50 cm$^3$) and the acidic aqueous portion was basified with solid sodium carbonate and extracted with dichloromethane (100 cm$^3$). The combined organic extracts were dried (Na$_2$SO$_4$) and the solvent was removed under reduced pressure to afford the title compound as a colourless oil.
B: The title compound was prepared from 2-(N-benzylmethylamino)methyl-1-(4-trifluoromethylphenyl)-3,4-dihydro-2H-napthalen-1-ol according to the procedures described in Examples 1 and 25. It was isolated as a white solid; m. p. 163–166° C.; positive ion ESI (M+H)$^+$ 378.0.

Example 28
cis-N-Methyl-N-(1,6-diphenyl-1,2,3,4-tetrahydronaphthalen-2-ylmethyl) aminomethylcarboxylic acid hydrochloride.

A: cis-2-(N-Benzylmethylamino)methyl-6-trifluoromethanesulfonyl-1-phenyl-1,2,3,4-tetrahydronaphthalene A solution of cis-2-(N-benzyl methylamino)methyl-6-hydroxy-1-phenyl-1,2,3,4-tetrahydronaphthalene (prepared as described in Example 1 and Example 32A; 3.23 g) in pyridine (15 cm$^3$) was cooled in an ice-bath. Trifluoromethanesulfonic anhydride (1.68 cm$^3$) was added dropwise to this solution and the resultant mixture was stirred at 0° C. for 5 min before being allowed to warm to room temperature. The mixture was then stirred at this temperature for 18 h, before being poured into water (90 cm$^3$). The resulting mixture was extracted with diethyl ether (2×100 cm$^3$) and the combined extracts were dried (Na$_2$SO$_4$). The solvent was removed under reduced pressure to afford a gum (4.83 g) which was purified by column chromatography [silica, eluting with toluene-ethyl acetate (19:1)] to yield the title compound as a gum (4.10 g); positive ion ESI (M+H)$^+$ 490.4.

B: cis-2-(N-Benzylmethylamino)methyl-1,6-diphenyl-1,2,3,4-tetrahydronaphthalene

Benzene boronic acid (301 mg), tetrakis(triphenylphosphine)palladium(0) (65 mg), lithium chloride (238 mg) and aqueous sodium carbonate solution (2 M, 2.25 cm$^3$) were added to a stirred solution of cis-2-(N-benzylmethylamino)methyl-6-trifluoromethanesulfonyl-1-phenyl-1,2,3,4-tetrahydronaphthalene (1.1 g) in 1,2-dimethoxyethane (60 cm$^3$) under an atmosphere of nitrogen. The stirred mixture was heated at 90° C. for 46 h before being allowed to cool to room temperature. Water (100 cm$^3$) and ethyl acetate (100 cm$^3$) were added and the organic layer was washed with water (3×100 cm$^3$), dried (Na$_2$SO$_4$), and the solvent was removed under reduced pressure. The crude product (908 mg) was purified by column chromatography [silica, eluting with toluene-ethyl acetate (19:1)] to afford the title compound as a gum (452 mg); positive ion ESI (M+H)$^+$ 417.9.

C: The title compound (Example 28) was prepared from cis-2-(N-benzylmethylamino)methyl-1,6-diphenyl-1,2,3,4-tetrahydronaphthalene according to the procedure described in Examples 1 and 25. However, in this case once the hydrolysis reaction was complete, hydrochloric acid (2 M, 5 cm$^3$) was added and the mixture was then extracted with dichloromethane (50 cm$^3$) and then with a dichloromethane-ethyl alcohol mixture (1:1; 75 cm$^3$). This second extract was dried (Na$_2$SO$_4$) and the solvent was removed under reduced pressure to afford a solid. Crystallisation from ethyl alcohol-diethyl ether furnished the title compound as a white solid; m. p. 210–221° C.; positive ion ESI (M+H)$^+$ 386.2.

Example 29
cis-N-Methyl-N-[1-phenyl-6-(thien-2-yl)-1,2,3,4-tetrahydronaphthalen-2-ylmethyl] aminomethylcarboxylate hydrochloride.

A: cis-2-(N-Benzyl-N-methylamino)methyl-1-phenyl-6-(thien-2-yl)-1,2,3,4-tetrahydronaphthalene A mixture of cis-5-(N-benzyl-N-methylaminomethyl)-4-phenyl-4,5,6,7-tetrahydronaphthalene trifluoromethanesulphonate (prepared according to Example 28A; (960 mg), tetrakis(triphenylphosphine)palladium(0) (59 mg), lithium chloride (213 mg) aqueous sodium carbonate solution (2 M, 2.0 cm$^3$) and thiophene-2-boronic acid (276 mg) in 1,2-dimethoxyethane (57 cm$^3$) was heated to reflux under nitrogen for 24 h. The reaction was allowed to cool, diluted with water (150 cm$^3$) and extracted with ethyl acetate (4×50 cm$^3$), which was washed with water (2×50 cm$^3$), dried (Na$_2$SO$_4$) and the solvent was evaporated. The crude product was purified by column chromatography [silica, eluting with heptane-ethyl acetate (gradient 4:1 to 1:1)] to afford the title compound as pale yellow crystals (762 mg); positive ion ESI (M+H)$^+$ 424.2.

B: cis-2-(N-Methylamino)methyl-1-phenyl-6-(thien-2-yl)1,2,3,4-tetrahydronaphthalene hydrochloride To a solution of cis-2-(N-benzyl-N-methylamino)methyl-1-phenyl-1,2,3,4-tetrahydro-6-(2-thienyl)naphthalene (727 mg) in dichloromethane (75 cm$^3$) which was being maintained at 0° C. under nitrogen was added 1-chloroethylchloroformate (0.208 cm$^3$) dropwise. The mixture was then allowed to warm to room temperature, before being heated to reflux. After approximately 2 h analysis of the reaction mixture indicated complete consumption of the starting material. The dichloromethane was evaporated and the residue was then taken up into methyl alcohol and heated to reflux for 1 h. The solvent was evaporated to afford the title compound which was used in the next reaction without further purification; positive ion ESI (M+H)$^+$ 334.2.

C: To a solution of ethyl cis-N-methyl-N-[6-(thien-2-yl)-1-phenyl-1,2,3,4-tetrahydronaphthalen-2-ylmethyl] aminomethylcarboxylate (prepared from the compound under B using procedures as described in Process 1) in ethyl alcohol was added aqueous sodium hydroxide solution (2 M, 0.55 cm$^3$) and the reaction was allowed to stir at room temperature. After 2 h the reaction was incomplete so a further portion of aqueous sodium hydroxide solution (as above) was then added and the mixture was heated to reflux overnight. Upon cooling, it was partitioned between hydrochloric acid (5 M) and a mixture of dichloromethane and chloroform (4:1). The insoluble material that remained was isolated by filtration to afford the title compound ((Example 29; 346 mg). Positive ion ESI (M+H)$^+$ 392.0.

Example 30
cis-N-Methyl-N-(6-cyano-1-phenyl-1,2,3,4-tetrahydronaphthalen-2-ylmethyl) aminomethylcarboxylic acid hydrochloride A: Methyl 1-phenyl-2-[methyl(phenylmethyl)aminomethyl]-3,4-dihydronaphthalene-6-carboxylic acid methyl ester A mixture of 2-(N-benzylmethylamino)methyl-6-bromo-1-phenyl-3,4-dihydronaphthalene (11.44 g; prepared according Process 1), 1,3-bis(diphenylphosphino)-propane (229 mg), palladium(II) acetate (185 mg), triethylamine (5.55 g), methyl alcohol (45 cm$^3$) and dimethyl sulfoxide (100 cm$^3$) was stirred vigorously until all the particles had dissolved. A stream of carbon monoxide gas (Caution! Highly toxic!) was passed through the solution for 2–3 min. The mixture was then placed under a positive pressure of carbon monoxide and heated to 100° C. in a sealed reaction bomb. After stirring for 4 h the mixture was cooled and water (400 cm$^3$) was added. The aqueous component was extracted with diethyl ether (3×150 cm$^3$) and the combined extracts were dried (Na$_2$SO$_4$) and filtered. The solvent was evaporated under reduced pressure to give a mixture of the title compound and the starting bromo-compound. This mixture was resolved by column chromatography [silica, eluting with petroleum ether (b.p. 40–60° C.)-ethyl acetate (9:1)] to afford the title compound (4.20 g) and the starting bromo compound (3.0 g).

B: Methyl 1-phenyl-2-(methylaminomethyl)-1,2,3,4-tetrahydronaphthalene-6-carboxylate To a mixture of 1-phenyl-2-[methyl(phenylmethyl)aminomethyl]-3,4-dihydronaphthalene-6-carboxylic acid methyl ester (4.20 g), methyl alcohol (120 cm³) and hydrochloric acid (5 M, 2.4 cm³) was added palladium on charcoal (5%, 500 mg). The resulting suspension was stirred at 50° C. under a hydrogen atmosphere (5 atm) for 18 h. Upon cooling the mixture was filtered through a pad of Dicalite® and the solvent was evaporated under reduced pressure to afford the title compound (3.49 g, 95%) as a white powder.

C: Methyl 1-phenyl-2-[methyl(phenylmethyl)aminomethyl]-1,2,3,4-tetrahydronaphthalene carboxylate To a mixture of cesium carbonate (7.04 g), methyl 1-phenyl-2-(methylaminomethyl)-1,2,3,4-tetrahydronaphthalene-6-carboxylate (3.41 g) and N,N-dimethylformamide (30 cm³) was added benzyl bromide (1.28 cm³). The mixture was warmed to 80° C. and stirred for 2 h. Upon cooling to room temperature, water (200 cm³) was added and the aqueous component was extracted with diethyl ether (2×100 cm³). The combined extracts were washed with water (75 cm³), dried ($Na_2SO_4$), filtered and solvent evaporated under reduced pressure to give a brown oil. The crude product was purified by column chromatography [silica, eluting with dichloromethane-methyl alcohol (19:1)] to afford the title compound (3.46 g) as a yellow oil which solidified on standing.

D: 1-Phenyl-2-[methyl(phenylmethyl)aminomethyl]-1,2,3,4-tetrahydronaphthalene carboxamide To a stirred mixture of 1-phenyl-2-[methyl(phenylmethyl)aminomethyl]-1,2,3,4-tetrahydronaphthalene carboxylic acid methyl ester (1.53 mg), formamide (577 mg) and N,N-dimethylformamide (5 cm³), being maintained at 100° C. under a nitrogen atmosphere, was added dropwise, via syringe, over a period of 20 min a solution sodium methoxide in methyl alcohol (0.5 M, 5 cm³). After 2.5 h the reaction had not gone to completion so further portions of formamide (577 mg) and sodium methoxide in methyl alcohol (0.5 M, 5 cm³) were added and the mixture was stirred at 100° C. under a nitrogen atmosphere for a further 2 h. The mixture was then allowed to cool to room temperature and water (50 cm³) was added. It was then extracted into diethyl ether (3×50 cm³) and the combined extracts dried ($Na_2SO_4$), filtered and the solvent evaporated under reduced pressure. The residue was purified by column chromatography [silica, eluting with dichloromethane-methyl alcohol (24:1)] to afford the title compound (927 mg) as a white foam.

E: 2-(N-Benzylmethylamino)methyl-6-cyano-1-phenyl-1,2,3,4-tetrahydronaphthalene

To a solution of 1-phenyl-2-[methyl(phenylmethyl)aminomethyl]-1,2,3,4-tetrahydronaphthalene carboxamide (588 mg, 1.53 mmol) in anhydrous N,N-dimethylformamide (5 cm³) under an argon atmosphere was added phosphorus oxychloride (0.429 cm³, 4.6 mmol). The mixture was warmed to 80° C. and stirred for 3 h. Upon cooling, water (20 cm³) was added and the mixture was basified with saturated aqueous sodium carbonate solution (20 cm³). The aqueous component was extracted with diethyl ether (3×50 cm³) and the combined extracts dried ($Na_2SO_4$), filtered and the solvent evaporated under reduced pressure. The residue was purified by column chromatography [silica, eluting with petroleum ether (b. p. 40–60° C.)-ethyl acetate (2:1)] to afford the title compound (450 mg) as a white solid.

F: cis-N-Methyl-N-(6-cyano-1-phenyl-1,2,3,4-tetrahydronaphthalen-2-ylmethyl) aminomethylcarboxylic acid hydrochloride Prepared from 2-(N-benzylmethylamino)methyl-6-cyano-1-phenyl-3,4-dihydronaphthalene using process steps as described in Scheme 1; m. p. 197° C. (decomp.); positive ESI (M+H)⁺ 335.2.

Example 31 cis-N-Methyl-N-[6-(methoxycarbonyl)-1-phenyl-1,2,3,4-tetrahydronaphthalen-2-ylmethyl] aminomethylcarboxylic acid hydrochloride salt A: Benzyl cis-N-methyl-N-[6-(methoxycarbonyl)-1-phenyl-1,2,3,4-tetrahydronaphthalen-2-ylmethyl] aminomethylcarboxylate To a mixture of cis-6-(methoxycarbonyl)-2-methylaminomethyl-1-phenyl-1,2,3,4-tetrahydronaphthalene hydrochloride (0.23 g; prepared as described in Example 30), cesium carbonate (0.48 g) and N,N-dimethylformamide (3 cm³) was added benzyl bromoacetate (0.11 cm³) and the resulting mixture was then stirred with heating at 85° C. for 4 h. The reaction was allowed to cool to room temperature and water (20 cm³) added. The resulting aqueous mixture was extracted with diethyl ether (2×20 cm³) and the combined organic extracts were washed with water (2×20 cm³), dried ($Na_2SO_4$) and the solvent was evaporated under reduced pressure. The crude product (0.29 g) was purified by column chromatography [silica, eluting with petroleum ether (b. p. 40–60° C.)-ethyl acetate (9:1)] to afford the title compound (0.20 g).

B: To a mixture of benzyl cis-N-methyl-N-[6-(methoxycarbonyl)-1-phenyl-1,2,3,4-tetrahydronaphthalen-2-ylmethyl] aminomethylcarboxylate (0.2 g), methyl alcohol (5 cm³) and hydrochloric acid (5 M, 0.1 cm³) was added palladium on charcoal (10%, 0.02 g). The reaction was stirred under an atmosphere of hydrogen (approx. 1.0 atm) at ambient temperature for 6 h. The catalyst was then removed by filtration through a Dicalite® pad and the solvent removed under reduced pressure. The product was crystallised from methyl alcohol-diethyl ether to yield the title compound (0.12 g) as a white solid; m. p. 166–171° C.; positive ion ESI (M+H)⁺ 368.0.

Example 32 cis-N-Methyl-N-[6-cyclohexyloxy-1-phenyl-1,2,3,4-tetrahydronaphthalen-2-ylmethyl] aminomethylcarboxylic acid hydrochloride A: 2-(N-Benzylmethylamino)methyl-6-hydroxy-1-phenyl-3,4-dihydronaphthalene To a solution of 2-(N-benzylmethylamino)methyl-6-methoxy-1-phenyl-3,4-dihydronaphthalene (0.375 g; prepared according to Process 1) in dichloromethane (15 cm³) being stirred at 0° C. under nitrogen was added a solution of boron tribromide in dichloromethane (1 M, 2.2 cm³). The resulting solution was stirred at 0° C. for 30 min and then at room temperature for 1.5 h. Methyl alcohol (5 cm³) was added and the solvents were removed under reduced pressure. The residue was treated with hydrochloric acid (6 M, 2 cm³) and dichloromethane (4 cm³) and stirred at room temperature for 30 min. The mixture was basified with potassium carbonate, diluted with water (50 cm³), and extracted with dichloromethane (3×25 cm³). The combined organic extracts were washed with brine (25 cm³), dried ($MgSO_4$), and the solvent was removed under reduced pressure. The crude product was purified by column chromatography [silica, eluting with ethyl acetate-heptane (1:1)] to yield the title compound (0.202 g) as a brown oil.

B: 2-(N-benzylmethylamino)methyl-6-cyclohexyloxy-1-phenyl-3,4-dihydronaphthalene To a mixture of 2-(N-benzylmethylamino)methyl-6-hydroxy-1-phenyl-3,4-dihydronaphthalene (0.53 g), cyclohexanol (0.26 cm³), triphenylphosphine (0.579 g) and tetrahydrofuran (20 cm³), was added diethyl azodicarboxylate (0.35 cm³) at room temperature. After stirring for 5 h the solvent was removed under reduced pressure. The crude product was purified by column chromatography [silica, eluting with ethyl acetate-heptane (1:4)] to yield the title compound (0.442 g) as a yellow oil.

C: The title compound was prepared from 2-(N-benzylmethylamino)methyl-6-cyclohexyloxy-1-phenyl-3,4-dihydronaphthalene according to Process 1; m. p. >210° C. (decomp.); positive ion ESI (M+H)⁺ 408.2.

Example 33
cis-N-Methyl-N-(6-benzyloxy-1-phenyl-1,2,3,4-tetrahydronaphthalen-2-ylmethyl) aminomethylcarboxylic acid hydrochloride A: cis-2-(N-Benzylmethylamino)methyl-6-methoxy-1-phenyl-1,2,3,4-tetrahydronaphthalene To a mixture of cis-6-methoxy-2-methylamino-1-phenyl-1,2,3,4-tetrahydronaphthalene (3.55 g, prepared according to Process 1), triethylamine (3.12 cm$^3$) and N,N-dimethylformamide (40 cm$^3$) was added benzyl bromide (1.60 cm$^3$). The mixture was warmed to 80° C. and stirred for 2 h. Upon cooling, the solvent was evaporated under reduced pressure to afford a brown oil. This was purified by column chromatography [silica, eluting with petroleum ether (b. p. 40–60° C.)-ethyl acetate (4:1)] to afford the title compound (3.52 g) as a light brown oil which solidified on standing.

B: cis-2-(N-Benzylmethylamino)methyl-6-hydroxy-1-phenyl-1,2,3,4-tetrahydronaphthalene This compound was prepared according to the procedure outlined in Example 32A, using cis-2-(N-benzylmethylamino)methyl-6-methoxy-1-phenyl-1,2,3,4-tetrahydronaphthalene as the starting material.

C: cis-2-(N-Benzylmethylamino)methyl-6-benzyloxy-1-phenyl-1,2,3,4-tetrahydronaphthalene To a mixture of cesium carbonate (1.09 g), cis-2-(N-benzylmethylamino)methyl-6-hydroxy-1-phenyl-1,2,3,4-tetrahydronaphthalene (600 mg) and N,N-dimethylformamide (10 cm$^3$) was added benzyl bromide (0.236 cm$^3$). The resulting mixture was warmed to 80° C. and stirred for 2 h. Upon cooling, water (50 cm$^3$) was added and the aqueous mass was extracted with ether (2×50 cm$^3$). The combined ether extracts were washed with water (30 cm$^3$), dried (Na$_2$SO$_4$), filtered and the solvent was evaporated under reduced pressure to afford a yellow oil. This was purified by column chromatography [silica, eluting with petroleum ether (b.p. 40–60° C.)-ethyl acetate (15:1)] to afford the title compound (538 mg; 72%) as a light yellow oil.

D: cis-6-Benzyloxy-2-methylamino-1-phenyl-1,2,3,4-tetrahydronaphthalene hydrochloride To a stirred, cooled (0° C.) solution of cis-2-(N-benzylmethylamino)methyl-6-benzyloxy-1-phenyl-1,2,3,4-tetrahydronaphthalene (264 mg) in dichloromethane (15 cm$^3$) was added 1-chloroethyl chloroformate (0.085 cm$^3$). After stirring at that temperature for 30 min the mixture was allowed to warm to room temperature and stirred for a further 1.5 h. The dichloromethane was evaporated under reduced pressure and methyl alcohol (20 cm$^3$) was added. The mixture was heated to reflux for 1.5 h before being allowed to cool to room temperature and evaporated to dryness. The resulting gum was triturated with ether to afford the title compound as a white solid (210 mg).

E: Ethyl cis-N-methyl-N-(6-benzyloxy-1-phenyl-1,2,3,4-tetrahydronaphthalen-2-ylmethyl) aminomethyl carboxylate Prepared from cis-6-benzyloxy-2-methylamino-1-phenyl-1,2,3,4-tetrahydronaphthalene hydrochloride using the method described in Process 1

F: Example 33 was prepared from ethyl cis-N-methyl-N-(6-benzyloxy-1-phenyl-1,2,3,4-tetrahydronaphthalen-2-ylmethyl) aminomethyl carboxylate using the method described in Example 25; m. p. 200–210° C.; positive ESI (M+H)$^+$ 416.2.

Methods similar to that of Example 33 were used to obtain:

Example 34
cis-N-Methyl-N-[6-(2,2-dimethylpropyloxy)-1-phenyl-1,2,3,4-tetrahydronaphthalen-2-ylmethyl] aminomethylcarboxylic acid hydrochloride; m. p. 151–155° C.; positive ESI (M+H)$^+$ 396.4; and

Example 35
cis-N-Methyl-N-(6-cyclopropylmethoxy-1-phenyl-1,2,3,4-tetrahydronaphthalen-2-ylmethyl) aminomethylcarboxylic acid hydrochloride; m. p. 173–177° C.; positive ion ESI (M+H)$^+$ 380.4.

Example 36
cis-N-Methyl-N-{5-phenyl-5,6,7,8-tetrahydronaphtho[2,3-d]-[1,3]dioxolemethyl} aminomethylcarboxylic acid hydrochloride A: 6,7-Dihydroxy-3,4-dihydro-2H-naphthalene-1-one A mixture of 6,7-dimethoxy-3,4-dihydro-2H-naphthalene-1-one (15.0 g) and 48% aqueous hydrobromic acid (60 cm$^3$) was heated under reflux for 18 h. Upon cooling to room temperature, water (100 cm$^3$) was added and the resulting aqueous mass was extracted with ethyl acetate (3×100 cm$^3$). The combined extracts were dried (Na$_2$SO$_4$), filtered and evaporated to dryness to leave a brown powder. This was recrystallised from acetonitrile to afford the title compound (9.4 g) as a red powder.

B: 7,8-Dihydro-6H-naphtho[2,3-d][1,3]dioxol-5-one

A mixture of 6,7-dihydroxytetralone (1 g), cesium carbonated (2.75 g), bromochloromethane (0.549 cm$^3$) and acetonitrile (20 cm$^3$) was heated to reflux with continual stirring for 4 h. Upon cooling, the resulting suspension was filtered through a pad of Dicalite® which was then washed further with ethyl acetate (50 cm$^3$). The crude product was then purified by column chromatography (silica, eluting with dichloromethane) to afford the title compound.

C: Example 36 was prepared from 7,8-dihydro-6H-naphtho[2,3-d][1,3]dioxol-5-one using the method described in Examples 1 and 25; m. p. 210° C. (decomp.); positive ion ESI (M+H)$^+$ 354.5.

Example 37
Sodium cis-N-methyl-N-[6-(2-phenoxyethoxy)-1-phenyl-1,2,3,4-tetrahydronaphthalen-2-ylmethyl] aminomethylcarboxylate A: 6-(2-Phenoxyethoxy)-3,4-dihydro-2H-naphthalen-1-one A mixture of 6-hydroxy-3,4-dihydro-2H-naphthalen-1-one (2.5 g), 2-phenoxyethyl bromide (3.4 g) and cesium carbonate (5.5 g) were stirred in N,N-dimethylformamide (15 cm$^3$) and heated at 100° C. for 2.5 h. The reaction mixture was allowed to cool to room temperature and then diluted with water (150 cm$^3$). The aqueous mixture was extracted with ethyl acetate (2×50 cm$^3$) and the organic extracts were washed with aqueous sodium hydroxide (1 M, 50 cm$^3$), water (50 cm$^3$) and then hydrochloric acid (2 M, 50 cm$^3$). The organic extracts were dried (Na$_2$SO$_4$) and the solvent removed under reduced pressure to afford the crude product which was suspended in diethyl ether and filtered to yield the title compound (3.2 g).

B: The title compound (Example 37) was prepared from 6-(2-phenoxyethoxy)-3,4-dihydro-2H-naphthalen-1-one according to the procedures described in Process 1; m. p. 109–113° C.; positive ion ESI (M+H)$^+$ 446.4.

Similarly obtained was:

Example 38
cis-N-Methyl-N-[6-(2-methoxyethoxy)-1-phenyl-1,2,3,4-tetrahydronaphthalen-2-ylmethyl] aminomethyl carboxylic acid hydrochloride; positive ion ESI (M+H)$^+$ 384.4.

Example 39
[2-cis-N-Methyl-N-(6-methoxy-1-phenyl-1,2,3,4-tetrahydronaphthalen-2-ylmethyl) amino]propionic acid hydrochloride A: Methyl-2-[cis-N-methyl-N-(6-methoxy-1-phenyl-1,2,3,4-tetrahydronaphthalen- 2-ylmethyl) amino]propionate To a mixture of cis-6-methoxy-2-methylaminomethyl-1-phenyl-1,2,3,4-tetrahydronaphthalene hydrochloride (1.00 g; prepared according to the procedures in Process 1), cesium carbonate (5.13 g) and N,N-dimethylformamide (20 cm$^3$) was added methyl-2-bromopropionate (0.35 cm$^3$) and the resultant mixture was stirred at 75° C. for 5 h. The reaction was then allowed to cool to room temperature and water (100 cm$^3$) was added. The resulting mixture was extracted with diethyl ether (2×100 cm$^3$) and the combined organic extracts were washed with water (100 cm$^3$), dried (Na$_2$SO$_4$) and the solvent was removed under reduced pressure. The crude product (1.11 g) was purified by column chromatography [basic alumina, eluting with toluene-hexane (1:1)] to afford the title compound as a gum (284 mg); positive ion ESI (M+H)$^+$ 368.4.

B: Example 39 was prepared from methyl-2-[cis-N-methyl-N-(6-methoxy-1-phenyl-1,2,3,4-tetrahydronaphthalen-2-ylmethyl) amino]propionate using methods describe in Example 25. The product was re-precipitated from dichloromethane-diethyl ether; m. p. 124–129° C.; positive ion ESI (M+H)$^+$ 354.4

Example 40
Benzyl cis-N-methyl-N-(6-methoxy-1-phenyl-1,2,3,4-tetrahydronaphth-2-ylmethyl) aminoacetate hydrochloride Lithium cis-N-methyl-N-[(6-methoxy-1-phenyl-1,2,3,4-tetrahydronaphth-2-yl)methyl]aminoacetate (prepared as described in Process 1, 249.8 mg), PyBrOP® (374.2 mg), 4-dimethylaminopyridine (67.5 mg), diisopropylethylamine (0.151 cm$^3$) and benzyl alcohol (0.079 cm$^3$) were dissolved in dry N,N-dimethylformamide (10 cm$^3$) and stirred overnight under nitrogen. The solvent was evaporated, and the residue taken up into water (25 cm$^3$) and extracted into dichloromethane (3×25 cm$^3$), which was dried (Na$_2$SO$_4$) and the solvent evaporated. The crude product was purified by column chromatography [silica, eluting with petroleum ether (b. p. 40–60° C.)-diethyl ether (1:1)] to afford the desired compound as its free base. This was taken up into dichloromethane and converted to the hydrochloride salt; positive ion ESI (M+H)$^+$ 430.3.

Example 41
cis-N-(6-Methoxy-1-phenyl-1,2,3,4-tetrahydronaphth-2-ylmethyl) amino carboxylic acid hydrochloride A: Benzyl cis-N-(6-methoxy-1-phenyl-1,2,3,4-tetrahydronaphth-2-ylmethyl) aminocarboxylate hydrochloride Benzyl cis-N-methyl-N-(6-methoxy-1-phenyl-1,2,3,4-tetrahydronaphth-2-ylmethyl) aminocarboxylate (prepared as described in Process 15; 96.9 mg) was dissolved in dichloromethane (25 cm$^3$) under an atmosphere of nitrogen, 1-chloroethyl chloroformate (0.254 cm$^3$) added and the mixture was heated to reflux for 72 h. The solvent was evaporated before a further portion of 1-chloroethyl chloroformate (0.254 cm$^3$) added and the mixture heated to 100° C. for a 7 days. Upon cooling, methyl alcohol (25 cm$^3$) was added and the mixture heated overnight. The solvent was then evaporated and the residue purified by high performance liquid chromatography [using a Supelco ABZ+ column; gradient elution with water-acetonitrile (95:5) through to neat acetonitrile all treated with 0.05% aqueous formic acid]. The fractions containing the product were treated with hydrochloric acid (5 M) and the volatiles were removed in vacuo to afford the title compound (37.4 mg); positive ion ESI (M+H)$^+$ 416.2.

B: Palladium on carbon (10%; 17.3 mg) was added to a solution of benzyl cis-N-(6-methoxy-1-phenyl-1,2,3,4-tetrahydronaphth-2-ylmethyl) aminocarboxylate hydrochloride (37.8 mg) in ethyl alcohol (10 cm$^3$) and hydrochloric acid (5 M, 1 cm$^3$) and the mixture stirred under hydrogen gas (1.5 bar) overnight. The mixture was filtered and the solvent evaporated. The residue was purified by high performance liquid chromatography (conditions as above) and appropriate fractions were treated with hydrochloric acid (5 M) to afford the title compound (10 mg); positive ion ESI (M+H)$^+$ 326.0.

Example 42
Resolution of Racemic Ethyl cis-N-methyl-N-(6-methoxy-1-phenyl-1,2,3,4-tetrahydronaphthalen-2-ylmethyl) aminomethylcarboxylate The racemate of Example 4, ethyl cis-N-methyl-N-(6-methoxy-1-phenyl-1,2,3,4-tetra-hydronaphthalen-2-ylmethyl) aminomethylcarboxylate, was prepared according to the procedures in Example 1, It (2.87 g) was then resolved by chiral HPLC using a Chiracel OJ 250×4.6 mm column (J T Baker), eluting with hexane-(2-propanol) (97:3) at a flow rate of 8 mL/min at room temperature. The fractions containing the two enantiomers (4.86 and 5.83 min) were combined and the volatiles were removed to afford the desired products.

Example (−)-4
(−)-Lithium cis-N-methyl-N-(6-methoxy-1-phenyl-1,2,3,4-tetrahydronaphthalen-2-ylmethyl) aminomethylcarboxylate.

(−)-Ethyl cis-N-methyl-N-(6-methoxy-1-phenyl-1,2,3,4-tetrahydronaphthalen-2-ylmethyl) aminomethylcarboxylate (0.58 g) was hydrolysed as described in Process 1 to afford the title compound (0.51 g) as an off-white solid; m. p. 173–184° C. (froth); positive ion ESI (M+H)$^+$ 346.2, [α]$_D$ (MeOH, c=9.26)−241.2°; and

Example (+)-4
(+)-Lithium cis-N-methyl-N-(6-methoxy-1-phenyl-1,2,3,4-tetrahydronaphthalen-2-ylmethyl) aminomethylcarboxylate (−)-Ethyl cis-N-methyl-N-(6-methoxy-1-phenyl-1,2,3,4-tetrahydronaphthalen-2-ylmethyl) aminomethylcarboxylate (0.58 g) was hydrolysed as described in Process 1 to afford the title compound (0.54 g) as an off-white solid; m. p. 146–154° C. (froth); positive ion ESI (M+H)$^+$ 346.2, [α]$_D$ (MeOH, c=8.53)+220.4°.

NOTE: Unless stated otherwise all other racemic esters were resolved using the chiral HPLC technique as exemplified in Example 42. The subsequent hydrolysis of the resulting levorotatory and dextrorotatory esters was done using the procedure described in Step 9 of Example 1. The following enantiomers were obtained:

Example (−)-23
(−)-Sodium cis-N-methyl-N-(6-methyl-1-phenyl-1,2,3,4-tetrahydronaphthalen-2-ylmethyl) aminomethylcarboxylate; prepared from the enantiomerically pure ester (retention time=4.27 min); [α]$_D$ (MeOH, c=1.51)=−228°.

Example (+)-23
(+)-Sodium cis-N-methyl-N-(6-methyl-1-phenyl-1,2,3,4-tetrahydronaphthalen-2-ylmethyl) aminomethylcarboxylate; prepared from the enantiomerically pure ester (retention time=5.23 min); [α]$_D$ (MeOH, c=1.59)=+226°.

Example (−)-17
(−)-Sodium cis-N-methyl-N-(6-phenoxy-1-phenyl-1,2,3,4-tetrahydronaphthalen-2-ylmethyl) aminomethylcarboxylate; prepared from the enantiomerically pure ester (retention time=14.40 min); [α]$_D$ (MeOH, c=1.29)=−188°.

Example (+)-17
(+)-Sodium cis-N-methyl-N-(6-phenoxy-1-phenyl-1,2,3,4-tetrahydronaphthalen-2-ylmethyl) aminomethylcarboxylate;

prepared from the enantiomerically pure ester (retention time=18.70 min); $[\alpha]_D$ (MeOH, c=1.67)=+192°.

Example 43

Resolution of Ethyl N-methyl-N-[1-(4-fluorophenyl)-6-trifluoromethyl-1,2,3,4-tetrahydronaphthalen-2-ylmethyl] aminomethylcarboxylate. The racemic ester was separated by chiral HPLC on a Chiracel OJ 250×4.6 mm column (J T Baker), eluting with hexane-ethyl alcohol-diisopropylethylamine (98:2:0.1); [(−)-enantiomer retention time=9.02 mins; (+)-enantiomer retention time=10.75 mins]; hydrolysis of the esters afforded:

Example (−)-8

(−)-Lithium N-methyl-N-[1-(4-fluorophenyl)-6-trifluoromethyl-1,2,3,4-tetrahydronaphthalen-2-ylmethyl] aminomethylcarboxylate. m. p. 161–164° C.; positive ESI (M+H)$^+$ 396.2, $[\alpha]_D$ (MeOH, c=4.17)=−208.2°; and Example (+)-8

(+)-cis-Lithium N-methyl-N-[1-(4-fluorophenyl)-6-trifluoromethyl-1,2,3,4-tetrahydronaphthalen-2-ylmethyl] aminomethylcarboxylate. m. p. 167–169° C.; positive ESI (M+H)$^+$ 396.2, $[\alpha]_D$ (MeOH, c=4.33)=+222.4°.

Example 44

Resolution of Lithium cis-N-methyl-N-[1-phenyl-6-(2,2-dimethylpropyloxy)-1,2,3,4-tetrahydronaphthalen-2-ylmethyl] aminomethylcarboxylate. The racemic ester was separated by chiral HPLC on a Daicel Chemical Industries Chiralpak AD column (25×2 cm) eluting with 2-propanol; (−)-enantiomer retention time 7.0 min, (+)-enantiomer retention time 8.0 min; hydrolysis of the esters afforded:

Example (−)-34

(−)-Lithium cis-N-methyl-N-[1-phenyl-6-(2,2-dimethylpropyloxy)-1,2,3,4-tetrahydronaphthalen-2-ylmethyl] aminomethylcarboxylate; m. p. 168–170° C.; positive ESI (M+H)$^+$ 396.2, $[\alpha]_D$ (MeOH, c=1.50)=−176.0°; and Example (+)-34

(+)-Lithium cis-N-methyl-N-[1-phenyl-6-(2,2-dimethylpropyloxy)-1,2,3,4-tetrahydronaphthalen-2-ylmethyl] aminomethylcarboxylate; m. p. 169–171° C.; positive ESI (M+H)$^+$ 396.1, $[\alpha]_D$ (MeOH, c=1.49)=+176.5°.

Example 45

Method for determination of glycine uptake in CHO cells heterologously expressing the human GlyT-1b transporter.
A: Cloning:
cDNA was generated by PCR according to the method described by Kim, K.-M. et al. Mol. Pharmacol. 1994, 45, 608–617. Sequence was verified by dideoxy sequencing using the ALF DNA sequencer™ (Pharmacia) and cloned into the expression construct pcDNA3 (Invitrogen).
B: Transfection:
Transfection of hGlyT-1b into CHO cells was performed using a standard calcium phosphate technique as described by Sambrook, J. et al. (1989) in *Molecular Cloning: A Laboratory Manual,* Cold Spring Harbor Laboratory, Cold Spring Harbor, N.Y.
C: Selection:
Stably transfected cells were selected for 1 week in growth medium containing 1 mg.cm$^{-3}$ Geneticin. Individual clones were picked for further analysis and positives passaged routinely as described below.
D: Culture conditions:
Cells stably expressing the hGlyT-1b gene were cultured at 37° C. in a 5% $CO_2$ atmosphere in DMEM—NUT.MIX. F12 with Glutamax-1 (Gibco) containing Geneticin (0.5 mg.cm$^{-3}$, Gibco) and supplemented with 10% Fetalclone II (Hyclone). Maintenance culture was carried out in standard 80 cm$^2$ ventilated flasks (2 m$^{-6}$ filter, Nunc) and cells were subcultured by trypsinisation (Sigma) when confluent.
E: Assay Procedure:
Cells for uptake studies were plated in 96 well plates (17,000 cells per well) in the absence of Geneticin and cultured for 48 h before use. To measure glycine transport, cells were washed twice with Hanks' balanced salt solution (HBSS) pre-warmed to 37° C. and excess fluid removed before addition of test compounds dissolved in 0.200 cm$^3$ HBSS. Plates were incubated at 37° C. for 5 minutes before addition of [$^3$H]glycine (0.050 cm$^3$, 150 M$^{-6}$, 248 Bq.nmol$^-$$_1$, NEN) and incubation continued for a further 10 minutes. Uptake was terminated by washing cells with ice-cold HBSS before removal of excess fluid and addition of 0.200 cm$^3$ scintillation cocktail to each well. Plates were sealed with adhesive film, shaken to ensure samples were homogenous before scintillation counting in a plate counter.
F: Data Analysis:
Data were analysed using standard curve fitting procedures to produce a $pIC_{50}$ value for active compounds (where $pIC_{50}$ is the negative logarithm of the concentration of test compound causing 50% inhibition of uptake).
G: Results:
The compounds of the invention selectively inhibit the glycine transport by the human GlyT-1b transporter as compared to the human GlyT-2 transporter (the molecular cloning and functional expression of the human GlyT-2 transporter is described by Morrow, J. A. et al. FEBS letters 1998, 439, 334–340. The $pIC_{50}$ values of the racemic materials and of the levorotatory enantiomers of the compounds described in Examples 4, 8, 17, 23 and 34 (the chiral separation of which is described in Examples 42–44) are given in Table I.

TABLE I

Inhibition of glycine transport by hGlyT-1

| EXAMPLE | COMPOUND | $pIC_{50}$ |
|---|---|---|
| (+/−)-4 | (+/−)-Lithium cis-N-methyl-N-(6-methoxy-1-phenyl-1,2,3,4-tetrahydronaphthalen-2-ylmethyl) aminomethylcarboxylate | 6.3 |
| (−)-4 | (−)-Lithium cis-N-methyl-N-(6-methoxy-1-phenyl-1,2,3,4-tetrahydronaphthalen-2-ylmethyl) aminomethylcarboxylate | 6.8 |
| (+/−)-8 | (+/−)-Lithium N-methyl-N-[1-(4-fluorophenyl)-6-trifluoromethyl-1,2,3,4-tetrahydronaphthalen-2-ylmethyl] aminomethylcarboxylate | 6.9 |

TABLE I-continued

Inhibition of glycine transport by hGlyT-1

| EXAMPLE | COMPOUND | pIC$_{50}$ |
|---|---|---|
| (−)-8 | (−)-Lithium N-methyl-N-[1-(4-fluorophenyl)-6-trifluoromethyl-1,2,3,4-tetrahydronaphthalen-2-ylmethyl] aminomethylcarboxylate | 7.3 |
| (+/−)-17 | (+/−)-Sodium cis-N-methyl-N-(6-phenoxy-1-phenyl-1,2,3,4-tetrahydronaphthalen-2-ylmethyl) aminomethylcarboxylate | 6.8 |
| (−)-17 | (−)-Sodium cis-N-methyl-N-(6-phenoxy-1-phenyl-1,2,3,4-tetrahydronaphthalen-2-ylmethyl) aminomethylcarboxylate | 7.0 |
| (+/−)-23 | (+/−)-Sodium cis-N-methyl-N-(6-methyl-1-phenyl-1,2,3,4-tetrahydronaphthalen-2-ylmethyl) aminomethylcarboxylate | 6.6 |
| (−)-23 | (−)-Sodium cis-N-methyl-N-(6-methyl-1-phenyl-1,2,3,4-tetrahydronaphthalen-2-ylmethyl) aminomethylcarboxylate | 6.9 |
| (+/−)-34 | (+/−)-Lithium cis-N-methyl-N-[1-phenyl-6-(2,2-dimethylpropyloxy)-1,2,3,4-tetrahydronaphthalen-2-ylmethyl] aminomethylcarboxylate | 6.6 |
| (−)-34 | (−)-Lithium cis-N-methyl-N-[1-phenyl-6-(2,2-dimethylpropyloxy)-1,2,3,4-tetrahydronaphthalen-2-ylmethyl] aminomethylcarboxylate | 6.6 |

What is claimed is:

1. An aminomethylcarboxylic acid derivative having the general formula I

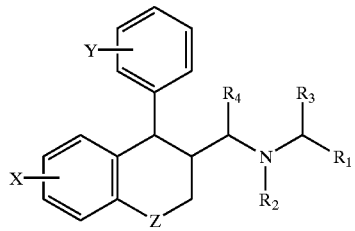

Formula I wherein

Z is $(CH_2)_n$, O, S, SO, $SO_2$ or N—$R_5$;

n is 0, 1 or 2;

X represents 1–3 substituents independently selected from hydrogen, halogen, $(C_{1-6})$alkyloxy, $(C_{3-6})$cycloalkyloxy, $(C_{6-12})$aryloxy, $(C_{6-12})$aryl, thienyl, $SR_6$, $SOR_6$, $SO_2R_6$, $NR_6R_6$, $NHR_6$, $NH_2$, $NHCOR_6$, $NSO_2R_6$, CN, $COOR_6$ and $(C_{1-4})$alkyl, optionally substituted with halogen, $(C_{6-12})$aryl, $(C_{1-6})$alkyloxy or $(C_{6-12})$aryloxy; or 2 substituents at adjacent positions together represent a fused $(C_{5-6})$aryl group, a fused $(C_{5-6})$cycloalkyl ring or O—$(CH_2)_m$—O; m is 1 or 2;

Y represents 1–3 substituents independently selected from hydrogen, halogen, $(C_{1-4})$alkyloxy, $SR_6$, $NR_6R_6$ and $(C_{1-4})$alkyl, optionally substituted with halogen;

$R_1$ is $COOR_7$ or $CONR_8R_9$;

$R_2$ and $R_6$ are $(C_{1-4})$alkyl;

$R_3$, $R_4$ and $R_5$ are independently hydrogen or $(C_{1-4})$alkyl;

$R_7$, $R_8$ and $R_9$ are independently hydrogen, $(C_{1-4})$alkyl, $(C_{6-12})$aryl or arylalkyl;

or a pharmaceutically acceptable salt thereof.

2. The aminomethylcarboxylic acid derivative of claim 1 wherein Z is $(CH_2)_n$ and n is 1.

3. The aminomethylcarboxylic acid derivative of claim 2, wherein $R_2$ is methyl, and $R_3$ and $R_4$ are each hydrogen.

4. The aminomethylcarboxylic acid derivative of claim 3, wherein $R_1$ is $COOR_7$.

5. The aminomethylcarboxylic acid derivative of claim 1 having the cis-configuration.

6. An aminomethylcarboxylic acid derivative according to claim 1 selected from the following levorotatory enantiomers:

(−)-Lithium cis-N-methyl-N-(6-methoxy-1-phenyl-1,2,3,4-tetrahydronaphthalen-2-ylmethyl) aminomethylcarboxylate;

(−)-Sodium cis-N-methyl-N-(6-methyl-1-phenyl-1,2,3,4-tetrahydronaphthalen-2-ylmethyl) aminomethylcarboxylate;

(−)-Sodium cis-N-methyl-N-(6-phenoxy-1-phenyl-1,2,3,4-tetrahydronaphthalen-2-ylmethyl) aminomethylcarboxylate;

(−)-Lithium N-methyl-N-[1-(4-fluorophenyl)-6-trifluoromethyl-1,2,3,4-tetrahydronaphthalen-2-ylmethyl)aminomethylcarboxylate;

(−)-Lithium cis-N-methyl-N-[1-phenyl-6-(2,2-dimethylpropyloxy)-1,2,3,4-tetrahydronaphthalen-2-ylmethyl]aminomethylcarboxylate.

7. A pharmaceutical composition comprising a compound according to claim 1, or a pharmaceutically acceptable salt thereof, and a pharmaceutically acceptable auxiliary.

8. A process for preparing a pharmaceutical composition comprising admixing a compound according to claim 1, or a pharmaceutically acceptable salt thereof, and a pharmaceutically acceptable auxiliary.

9. A method for inhibiting glycine transport by the human GlyT-1b transporter in a patient, comprising administering thereto an effective amount of a compound of formula (I)

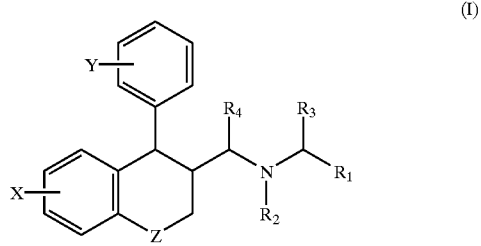

(I)

wherein:

Z is $(CH_2)_n$, O, S, SO, $SO_2$ or N—$R_5$;

n is 0, 1 or 2;

X represents 1–3 substituents independently selected from hydrogen, halogen, $(C_{1-6})$alkyloxy, $(C_{3-6})$ cycloalkyloxy, $(C_{6-12})$aryloxy, $(C_{6-12})$aryl, thienyl, $SR_6$, $SOR_6$, $SO_2R_6$, $NR_6R_6$, $NHR_6$, $NH_2$, $NHCOR_6$, $NHSO_2R_6$, CN, $COOR_6$ and $(C_{1-4})$alkyl, optionally substituted with halogen, $(C_{6-12})$aryl, $(C_{1-6})$alkyloxy or $(C_{6-12})$aryloxy; or 2 substituents at adjacent positions together forming a fused $(C_{5-6})$aryl group, a fused $(C_{5-6})$cycloalkyl ring or O—$(CH_2)_m$—O;

m is 1 or 2;

Y represents 1–3 substituents independently selected from hydrogen, halogen, $(C_{1-4})$alkyloxy, $SR_6$, $NR_6R_6$ and $(C_{1-4})$alkyl, optionally substituted with halogen;

$R_1$ is $COOR_7$ or $CONR_8R_9$;

$R_2$ and $R_6$ are $(C_{1-4})$alkyl;

$R_3$, $R_4$ and $R_5$ are independently hydrogen or $(C_{1-4})$alkyl;

$R_7$, $R_8$ and $R_9$ are independently hydrogen, $(C_{1-4})$alkyl, $(C_{6-12})$aryl or arylalkyl; or a pharmaceutically acceptable salt thereof.

10. The method of claim 9, wherein said compound selectively inhibits glycine transport by the human GlyT-1b transporter over glycine transport by the human GlyT-2 transporter.

11. The method of claim 9, wherein Z is $(CH_2)_n$ and n is 1.

12. The method of claim 11, wherein $R_2$ is methyl, and $R_3$ and $R_4$ are each hydrogen.

13. The method of claim 12, wherein $R_1$ is $COOR_7$.

14. The method of claim 9, wherein said compound is in the cis-configuration.

15. The method of claim 9, wherein said compound is selected from:

(−)-Lithium cis-N-methyl-N-(6-methoxy-1-phenyl-1,2,3,4-tetrahydronaphthalen-2-ylmethyl)aminomethylcarboxylate;

(−)-Sodium cis-N-methyl-N-(6-methyl-1-phenyl-1,2,3,4-tetrahydronaphthalen-2-ylmethyl)aminomethylcarboxylate;

(−)-Sodium cis-N-methyl-N-(6-phenoxy-1-phenyl-1,2,3,4-tetrahydronaphthalen-2-ylmethyl)aminomethylcarboxylate;

(−)-Lithium N-methyl-N-[1-(4-fluorophenyl)-6-trifluoromethyl-1,2,3,4-tetrahydronaphthalen-2-ylmethyl)aminomethylcarboxylate; and (−)-Lithium cis-N-methyl-N-[1-phenyl-6-(2,2-dimethylpropyloxy)-1,2,3,4-tetrahydronaphthalen-2-ylmethyl)aminomethylcarboxylate.

16. A method for treating a neurological or neuropsychiatric disorder in a patient comprising administering to the patient an effective amount of a compound of formula (I)

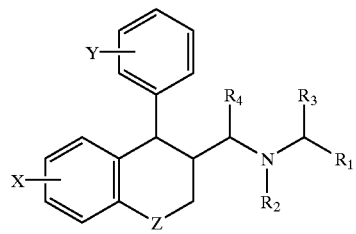

(I)

wherein:

Z is $(CH_2)_n$, O, S, SO, $SO_2$ or N—$R_5$;

n is 0, 1 or 2;

X represents 1–3 substituents independently selected from hydrogen, halogen, $(C_{1-6})$alkyloxy, $(C_{3-6})$cycloalkyloxy, $(C_{6-12})$aryloxy, $(C_{6-12})$aryl, thienyl, $SR_6$, $SOR_6$, $SO_2R_6$, $NR_6R_6$, $NHR_6$, $NH_2$, $NHCOR_6$, $NHSO_2R_6$, CN, $COOR_6$ and $(C_{1-4})$alkyl, optionally substituted with halogen, $(C_{6-12})$aryl, $(C_{1-6})$alkyloxy or $(C_{6-12})$aryloxy; or 2 substituents at adjacent positions together forming a fused $(C_{5-6})$aryl group, a fused $(C_{5-6})$cycloalkyl ring or O—$(CH_2)_m$—O—;

m is 1 or 2;

Y represents 1–3 substituents independently selected from hydrogen, halogen, $(C_{1-4})$alkyloxy, $SR_6$, $NR_6R_6$ and $(C_{1-4})$alkyl, optionally substituted with halogen;

$R_1$ is $COOR_7$ or $CONR_8R_9$;

$R_2$ and $R_6$ are $(C_{1-4})$alkyl;

$R_3$, $R_4$ and $R_5$ are independently hydrogen or $(C_{1-4})$alkyl;

$R_7$, $R_8$ and $R_9$ are independently hydrogen, $(C_{1-4})$alkyl, $(C_{6-12})$aryl or arylalkyl; or a pharmaceutically acceptable salt thereof.

17. The method of claim 16, wherein said disorder is schizophrenia, depression, dementia, impaired cognition, Alzheimer's disease, Parkinson's disease, Huntington's disease, muscle spasticity, myoclonus or epilepsy.

18. The method of claim 16, wherein Z is $(CH_2)_n$ and n is 1.

19. The method of claim 18, wherein $R_2$ is methyl, and $R_3$ and $R_4$ are each hydrogen.

20. The method of claim 19, wherein $R_1$ is $COOR_7$.

21. The method of claim 16, wherein said compound is in the cis-configuration.

22. The method of claim 16, wherein said compound is selected from:

(−)-Lithium cis-N-methyl-N-(6-methoxy-1-phenyl-1,2,3,4-tetrahydronaphthalen-2-ylmethyl)aminomethylcarboxylate;

(−)-Sodium cis-N-methyl-N-(6-methyl-1-phenyl-1,2,3,4-tetrahydronaphthalen-2-ylmethyl)aminomethylcarboxylate;

(−)-Sodium cis-N-methyl-N-(6-phenoxy-1-phenyl-1,2,3,4-tetrahydronaphthalen-2-ylmethyl)aminomethylcarboxylate;

(−)-Lithium N-methyl-N-[1-(4-fluorophenyl)-6-trifluoromethyl-1,2,3,4-tetrahydronaphthalen-2-ylmethyl)aminomethylcarboxylate; and (−)-Lithium cis-N-methyl-N-[1-phenyl-6-(2,2-dimethylpropyloxy)-1,2,3,4-tetrahydronaphthalen-2-ylmethyl)aminomethylcarboxylate.

* * * * *